United States Patent
Jung (10) Patent No.: US 10,660,779 B2
(45) Date of Patent: May 26, 2020

(54) MAGNET ASSEMBLY APPARATUS FOR TREATING OBESITY AND A METHOD FOR USING THE SAME

(71) Applicant: Sung Woong Jung, Seoul (KR)

(72) Inventor: Sung Woong Jung, Seoul (KR)

( * ) Notice: Subject to any disclaimer, the term of this patent is extended or adjusted under 35 U.S.C. 154(b) by 0 days.

(21) Appl. No.: 16/103,926

(22) Filed: Aug. 14, 2018

(65) Prior Publication Data
US 2020/0054470 A1 Feb. 20, 2020

(30) Foreign Application Priority Data

Jun. 29, 2017 (KR) .......... 10-2017-0082272

(51) Int. Cl.
*A61F 5/00* (2006.01)
*A61B 34/00* (2016.01)
*H01F 7/02* (2006.01)

(52) U.S. Cl.
CPC ............ *A61F 5/0046* (2013.01); *A61B 34/73* (2016.02); *A61F 5/0089* (2013.01); *H01F 7/02* (2013.01)

(58) Field of Classification Search
CPC ...... A61F 5/0036; A61F 5/004; A61F 5/0046; A61F 5/003; A61F 5/0013; H01F 7/02; A61B 34/73
See application file for complete search history.

(56) References Cited

U.S. PATENT DOCUMENTS

| | | | |
|---|---|---|---|
| 2007/0149994 A1* | 6/2007 | Sosnowski | A61F 5/003 606/192 |
| 2007/0276428 A1* | 11/2007 | Haller | A61F 5/0003 606/192 |
| 2008/0172079 A1 | 7/2008 | Birk | |
| 2010/0249822 A1* | 9/2010 | Nihalani | A61F 5/003 606/191 |
| 2016/0030220 A1* | 2/2016 | Weber | A61F 5/0036 606/192 |

* cited by examiner

*Primary Examiner* — Tan-Uyen T Ho
*Assistant Examiner* — Chima U Igboko
(74) *Attorney, Agent, or Firm* — Antonio Ha & U.S. Patent, LLC (57) ABSTRACT

A magnet assembly apparatus for obesity treatment and a use method of the same are disclosed. The magnet assembly apparatus for obesity treatment according to the present invention is a magnet assembly apparatus for obesity treatment which can be injected by an oral approach into the stomach of a patient. The magnet assembly apparatus comprises a first sphere having a first diameter and silicon-coated on the outside; and a second sphere having a second diameter bigger than the first diameter, which is a magnetic substance having a magnetic force of a predetermined value.

6 Claims, 10 Drawing Sheets

MAGNET ASSEMBLY APPARATUS FOR TREATING OBESITY AND A METHOD FOR USING THE SAME

CROSS-REFERENCE TO RELATED APPLICATION

This application claims priority to Korean Patent Application No. 10-2017-0082272, filed on Jun. 29, 2017, and all the benefits accruing therefrom under 35 U.S.C. § 119, the contents of which are herein incorporated by reference in their entireties.

BACKGROUND OF THE INVENTION

1. Field of the Invention

Exemplary embodiments of the present invention relate to a magnet assembly apparatus for obesity treatment and a method of using the same.

2. Description of the Related Art

In general, obesity refers to the excess weight of a person, which is pathologically referred to as obesity if the Body Mass Index (BMI) is over 30 as defined by the World Health Organization (WHO). In most cases, obesity means that the body weight is higher than normal, but even if the body weight is not too much, the high proportion of body fat among the constituents of the body is also called obesity. Therefore, the diagnosis is made by examining the visceral fat rate, the abdominal fat percentage, and the body fat percentage together with the simple weight.

With regard to obesity, social problems that can result from obesity, and secondary complications from excess fat, can be particularly serious problems, rather than problems caused by obesity itself. Obesity significantly increases the incidence of diabetes, hypertension, hyperlipidemia, arteriosclerosis, fatty liver and joint abnormalities, which are typical complications of obesity.

Generally, obesity treatment include surgical treatment and non-surgical treatment such as behavior therapy, meal treatment, exercise treatment, and drug treatment. For simply overweight patients, non-surgical treatment is likely to be successful in weight loss and weight maintenance, but surgical treatment should be considered for patients with 'extremely obesity'. 'Extremely obesity' is defined as the case of a BMI of more than 40 kg/m 2 or a BMI of more than 35 kg/m 2 with a coexisting disease due to obesity. 'Extremely obesity' causes not only changes body shape but also causes high mortality rates due to associated complications such as type 2 diabetes, hypertension, hypertrophic cardiomyopathy, heart failure, hyperlipidemia, gallstone disease, obstructive sleep apnea, asthma, hypopnea and degenerative arthritis. However, statistically, the results of non-surgical treatment (exercise, diet, various medications, etc.) of life-threatening extremely obesity patients are not good. And most of them may experience weight gain again within 5 years and suffer from side effects (especially drug side effects) of non-surgical treatment. So, surgical treatments are considered as the most effective method.

The most commonly performed operations are gastric banding, gastric bypass surgery, and sleeve gastrectomy. Gastric banding surgery is a procedure that purely restricts food intake by wrapping a band around the upper part of the stomach to reduce the capacity of the stomach. The gastric bypass surgery is a procedure that simultaneously restricts food intake and nutrition absorption. According to the gastric bypass surgery, the gastric volume is reduced to approximately 20 cc, and the remaining stomach and the proximal small intestine are then connected with the distal small intestine. Sleeve gastrectomy is a procedure to remove the greater curvature, which increases by food intake, so by decreasing the gastric capacity to achieve food intake restriction. There are many positive reports on safety and effectiveness, so this is becoming an increasingly common surgical procedure nowadays.

However, the above mentioned surgical treatments may cause side effects such as anastomotic leakage, atelectasis and pneumonia, intra-abdominal abscess, pancreatic leakage, intestinal obstruction due to bowel obstruction, etc. And the above mentioned surgical treatments may cause inconvenience such as hospitalization after surgery, an increase in medical expenses for postoperative complications, vomiting, diarrhea, abdominal hernia and infection, etc.

Currently, an end ball diet method has been proposed to solve the problems of such surgical treatments. This is a method to achieve weight loss effect by inserting a balloon (end ball) into the stomach using an endoscope and injecting air and physiological saline into the balloon to reduce stomach capacity.

In this regard. KR 10-2014-0067354A1 discloses a gastric balloon inserting device for inserting a balloon into the stomach and injecting air into the balloon to achieve the weight loss effect.

However, such an end ball diet method has the risk of causing the gastric balloon to burst in the stomach due to an external impact or the like. There is also a risk of injury on the stomach or esophagus cause the end ball has to be punctured by a needle for removing the end ball when the end ball is removed (usually 6 months after insertion).

The present invention has been made to solve the above-mentioned problems that previous surgical treatments and the end ball diet method for treating obesity had.

In particular, the present invention intends to provide a magnet assembly apparatus capable of treating obesity non-invasively without leaving a scar on the body of the patient.

In addition, the present invention provides a magnet assembly apparatus capable of treating and preventing obesity in a simple, convenient, and safe manner and enabling daily life immediately without requiring hospitalization as in the conventional surgical treatment or end ball method.

The present invention also provides a magnet assembly device capable of natural weight loss by suppressing appetite by increasing the feeling of fullness.

BRIEF SUMMARY OF THE INVENTION

Exemplary embodiments of the present invention provide a magnet assembly apparatus for treating obesity.

In an exemplary embodiment of a magnet assembly apparatus for obesity treatment which can be injected by an oral approach into the stomach of a patient, the apparatus comprises a first sphere having a first diameter and silicon-coated on the outside; and a second sphere having a second diameter bigger than the first diameter, which is a magnetic substance having a magnetic force of a predetermined value, wherein the first and the second spheres are gathered by mutual magnet force to form the magnet assembly apparatus having a size that does not pass through the pylorus, and when the magnet force of the second sphere is lost, the aggregation of the first sphere and the second sphere is released, and the first sphere is discharged to the outside of the body through the large intestine.

In the exemplary embodiment, the first diameter is 1.2 cm and the second diameter is 2 cm.

In the exemplary embodiment, the gathered first and second spheres are wrapped by a medical silicon net.

In the exemplary embodiment, the medical silicon net is formed of an automatically melting material in the body after a predetermined time.

In the exemplary embodiment, the second sphere comprises a battery and a magnetic force generating device inside, and when the set time comes, the voltage of the battery drops below the threshold voltage that generates a magnetic force capable of combining the first and second spheres.

In the exemplary embodiment, the second sphere comprises a holding portion formed protrude from the outer surface of the second sphere, and the holding portion can be caught by a forceps of an endoscope.

In the exemplary embodiment, the height of the holding portion is between 3.0 mm and 4.0 mm.

Exemplary embodiments of the present invention provide a use method of a magnet assembly apparatus for treating obesity.

In the exemplary embodiment, the method comprises injecting a first sphere configured to be a metal sphere and have a first diameter and silicon-coated on the outside; injecting a second sphere configured to be a magnetic substance having magnetic force of a predetermined value and configured to have a second diameter bigger than the first diameter, forming the magnet assembly apparatus configured to have a size that does not pass through the pylorus by agglomerating the first and the second spheres by mutual magnetic force, and wherein when set time passes, the magnetic force of the second sphere falls below a critical magnetic force capable of agglomerating the first sphere and the second sphere, when the aggregation state of the first sphere and the second sphere is released, the first sphere is discharged to the outside of the body through the large intestine.

According to the present invention as described above, it is possible to solve the problems of the conventional surgical treatment for obesity treatment and the problems of the end ball diet method.

Particularly, according to the present invention, it is possible to treat and prevent obesity easily, conveniently and safely in a non-invasive manner, and immediate daily life is possible without hospitalization like surgical treatment.

Further, according to the present invention, there is an advantage that weight loss can be achieved naturally by suppressing appetite by increasing the satiety feeling, and the yo-yo phenomenon can be minimized.

BRIEF DESCRIPTION OF THE DRAWINGS

The above and other features and advantages of the present invention will become more apparent by describing in detailed exemplary embodiments thereof with reference to the accompanying drawings, in which.

DETAILED DESCRIPTION OF THE INVENTION

The objects, features and advantages of the present invention described above will become more apparent from the following description of the embodiments with reference to the accompanying drawings.

The following specific structural or functional descriptions are merely illustrative for purposes of illustrating embodiments according to the concept of the present invention, and it is to be understood that the embodiments in accordance with the concepts of the present invention may be embodied in various forms, and it should not be construed as being limited to the examples described in the specification.

The embodiments according to the concept of the present invention can make various changes and have various forms, so that specific embodiments are illustrated in the drawings and described in detail in the present specification. However, it should be understood that it is not intended to limit the embodiments according to the concepts of the present invention to the particular forms disclosed, but includes all modifications, equivalents, and alternatives falling within the spirit and scope of the present invention.

Terms including ordinals, such as first, second, etc., may be used to describe various elements, but the elements are not limited by these terms. The terms are used only for the purpose of distinguishing one component from another.

It is understood that when one element is described as being "conmected" or "coupled" to another element, the element may be directly connected to another component, or there may be other element in between. In contrast, when an element is referred to as being "directly connected" or "directly coupled" to another element, it should be understood that there are no other elements in between.

Expression in the singular number include a plural forms unless the context clearly indicates otherwise.

In this application, when a component is referred to as being 'comprise' or 'include' another component, it is understood that it means that it can include other components as well, without excluding other components unless specifically stated otherwise.

It is apparent to those skilled in the art that the present invention may be embodied in other specific forms without departing from the essential characteristics thereof.

Hereinafter, exemplary embodiments of the present invention will be described in further detail with reference to the accompanying drawings. In the drawings, a same reference refers to a same element.

Figure 1A:
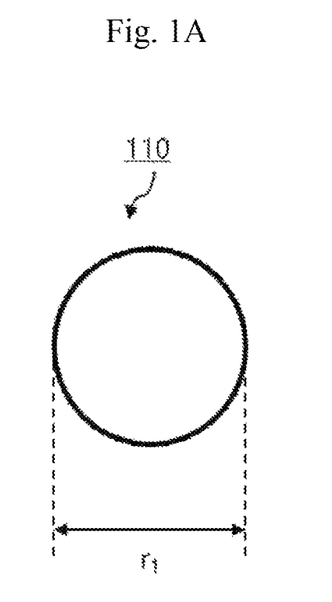
FIGS. 1A and 1B are views of a first sphere forming a magnet assembly apparatus according to an embodiment of the present invention.
Figure 1B:
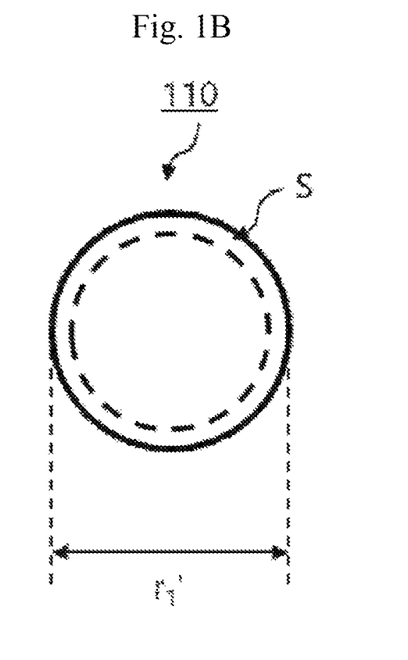
Figure 3A:
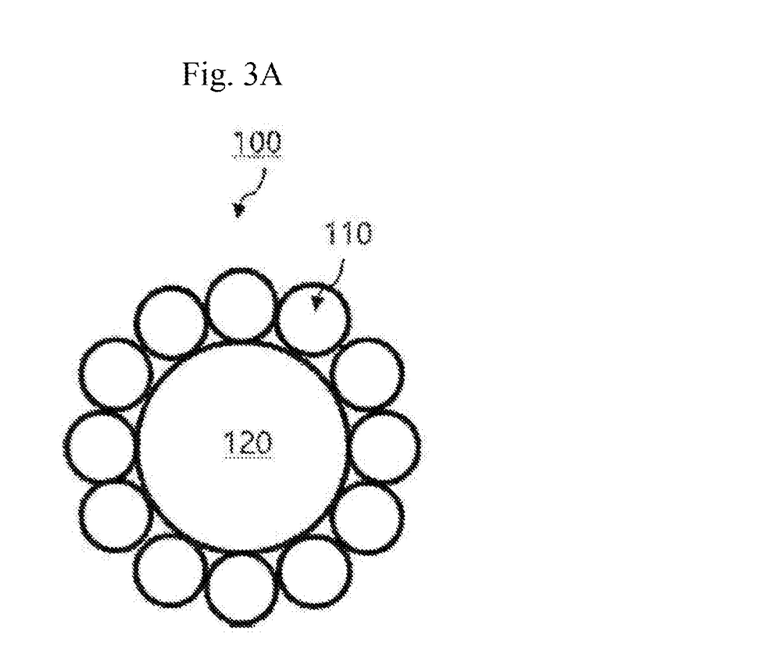
FIGS. 3A and 3B are views of a magnet assembly apparatus according to an embodiment of the present invention.
Figure 3B:
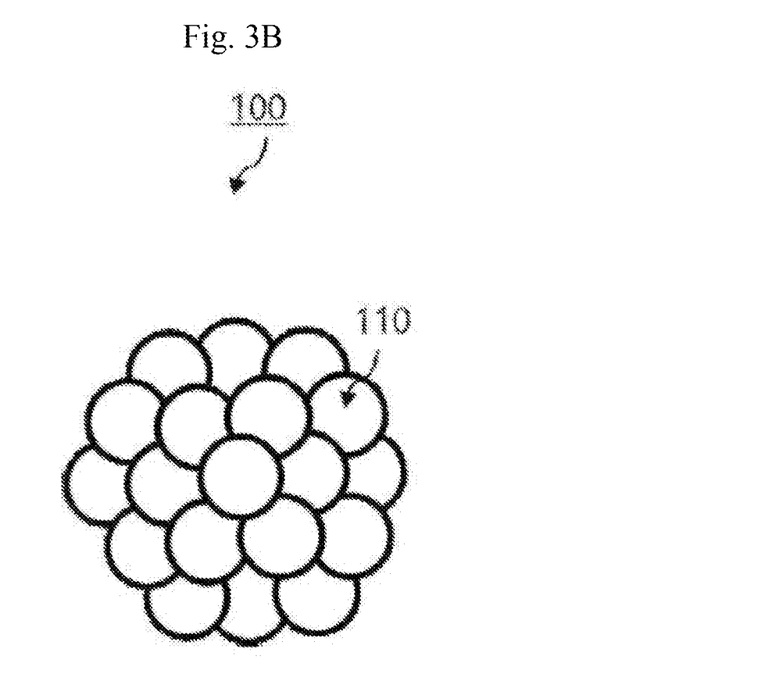
Figure 4:
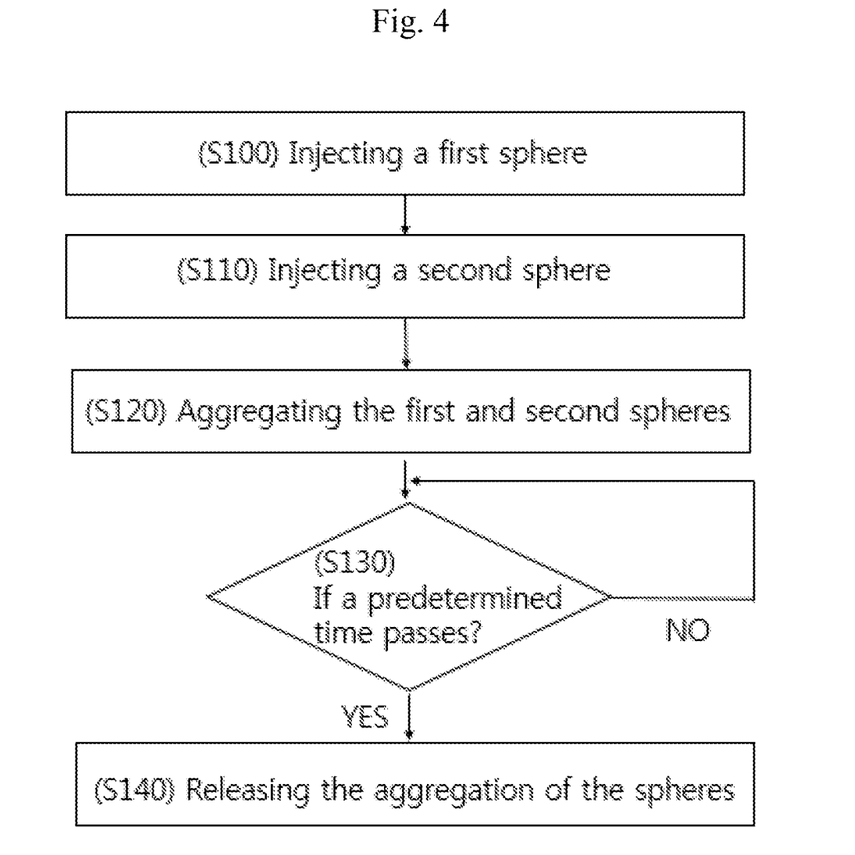
FIG. 4 is a flowchart of a method of using the magnet assembly apparatus according to another embodiment of the present invention.
Figure 5:
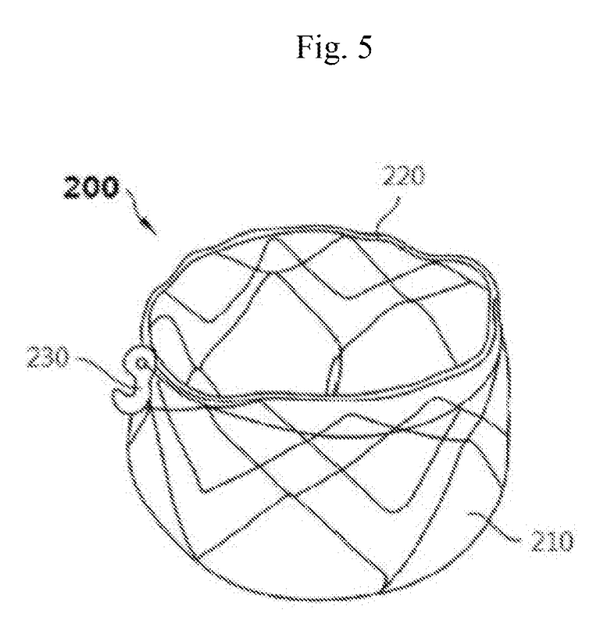
FIG. 5 is an exemplary view of a silicon net applied to a magnet assembly apparatus according to an embodiment of the present invention.

FIGS. 1A and 1B are views of a first sphere forming a magnet assembly apparatus according to an embodiment of the present invention. FIGS. 2A, 2B, 2C, 2D, and 2E are views of a second sphere forming a magnet assembly apparatus according to an embodiment of the present invention. FIGS. 3A and 3B are views of a magnet assembly apparatus according to an embodiment of the present invention. FIG. 4 is a flowchart of a method of using the magnet assembly apparatus according to another embodiment of the present invention. FIG. 5 is an exemplary view of a silicon net applied to a magnet assembly apparatus according to an embodiment of the present invention. FIGS. 6A, 6B, 6C, 6D, and 6E are schematic views illustrating a method of using the magnet assembly apparatus according to an embodiment of the present invention.

Hereinafter, a magnet assembly apparatus and a method of using the magnet assembly apparatus according to the present invention will be described in detail with reference to FIGS. 1 to 6.

A Magnet Assembly Apparatus

FIG. 1A and FIG. 1B are views for explaining a first sphere (110) constituting a magnet assembly apparatus according to an embodiment of the present invention. FIG. 1A shows the first sphere (110) without a silicon coating and FIG. 1B shows the silicon-coated first sphere (110). The first sphere (110) is preferably a metal sphere, more preferably a metal sphere of Fe component. The diameter ($r\_1$) of the first sphere (110) is smaller than the diameter of the human esophagus. Since the diameter of the adult esophagus is usually about 2 cm, the diameter of the first sphere (110) is preferably less than 2 cm, or more preferably 1.2 cm. Meanwhile, as shown in FIG. 1B, the first sphere (110) constituting the magnet assembly apparatus according to an embodiment of the present invention may be coated with the medical silicone (S). The silicon (S) is preferably coated on the outer surface of the first sphere (110) with a uniform thickness. In this case, it is preferable that the total diameter of the silicon-coated first sphere is less than 2 cm.

As described above, since the diameter ($r\_1$) of the first sphere or the total diameter ($r\_1^\wedge t$) of the silicon-coated first sphere is smaller than the diameter of the human esophagus, the patient can take the first sphere (110) by oral administration to send it to the stomach. The number of the first spheres (110) taken orally by the patient can be appropriately determined according to the physical condition of the patient, the degree of obesity, the target weight value, the target BMI, etc. That is, the patient can take orally at least one or more first spheres (110) based on his/her body condition, degree of obesity, target weight, etc.

Figure 2A:
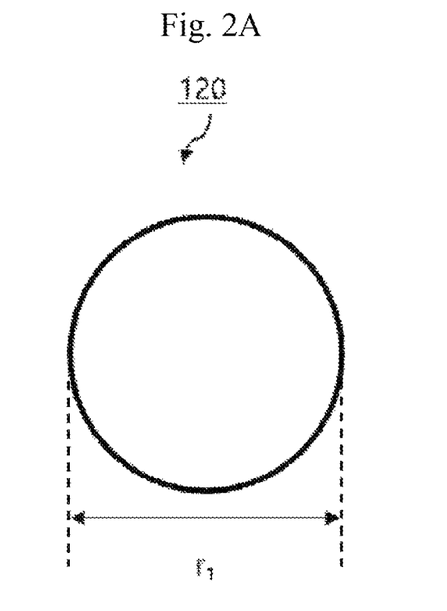
FIGS. 2A, 2B, 2C, 2D, and 2E are views of a second sphere forming a magnet assembly apparatus according to an embodiment of the present invention.
Figure 2B:
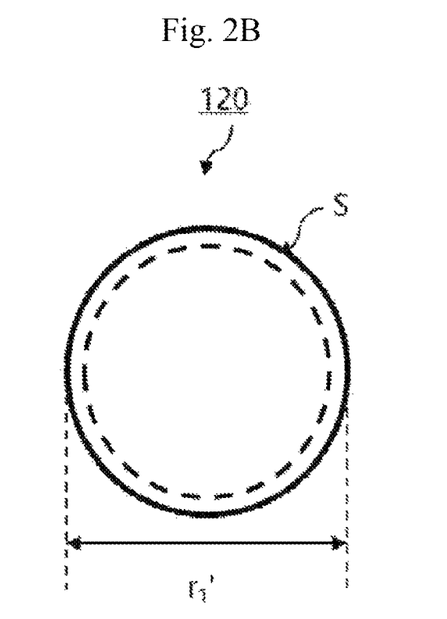

FIGS. 2A and 2B are views for explaining the second sphere (120) constituting a magnet assembly apparatus according to an embodiment of the present invention. FIG. 2A shows the second sphere (120) without the silicon coating and FIG. 2B shows the silicon-coated second sphere (120). The second sphere (120) may be a magnetic material having a magnetic force of a predetermined value and the diameter ($r\_2$) of the second sphere (120) is larger than the diameter ($r\_1$) of the first sphere (110) described above. As will be described later, the second sphere (120) can be inserted into a human stomach using an endoscope. Therefore, it is preferable that the diameter ($r\_2$) of the second sphere (120) does not exceed about 2 cm, which is the diameter of a typical human esophagus. Meanwhile, as shown in FIG. 2B, the second sphere (120) may be coated with a medical silicone (S) as well. The silicon (S) is preferably coated on the outer surface of the second sphere (120) with a uniform thickness. In this case, it is preferable that the total diameter ($r\_2^\wedge t$) of the silicon-coated second sphere is about 2 cm.

Figure 2C:
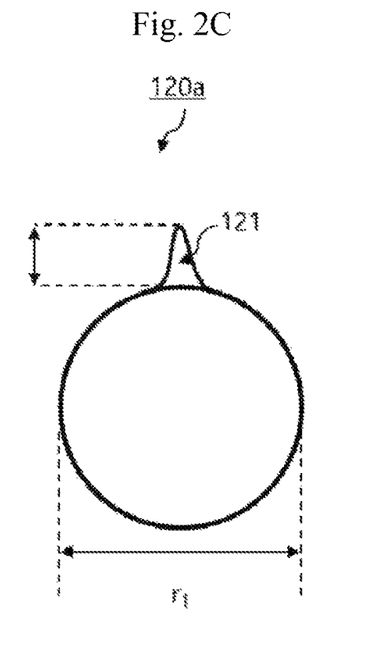
Figure 2D:
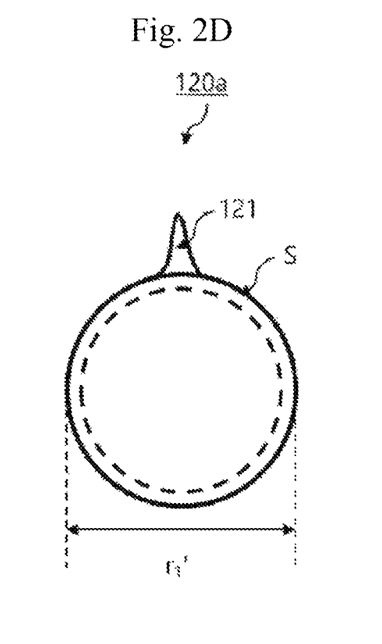
Figure 2E:
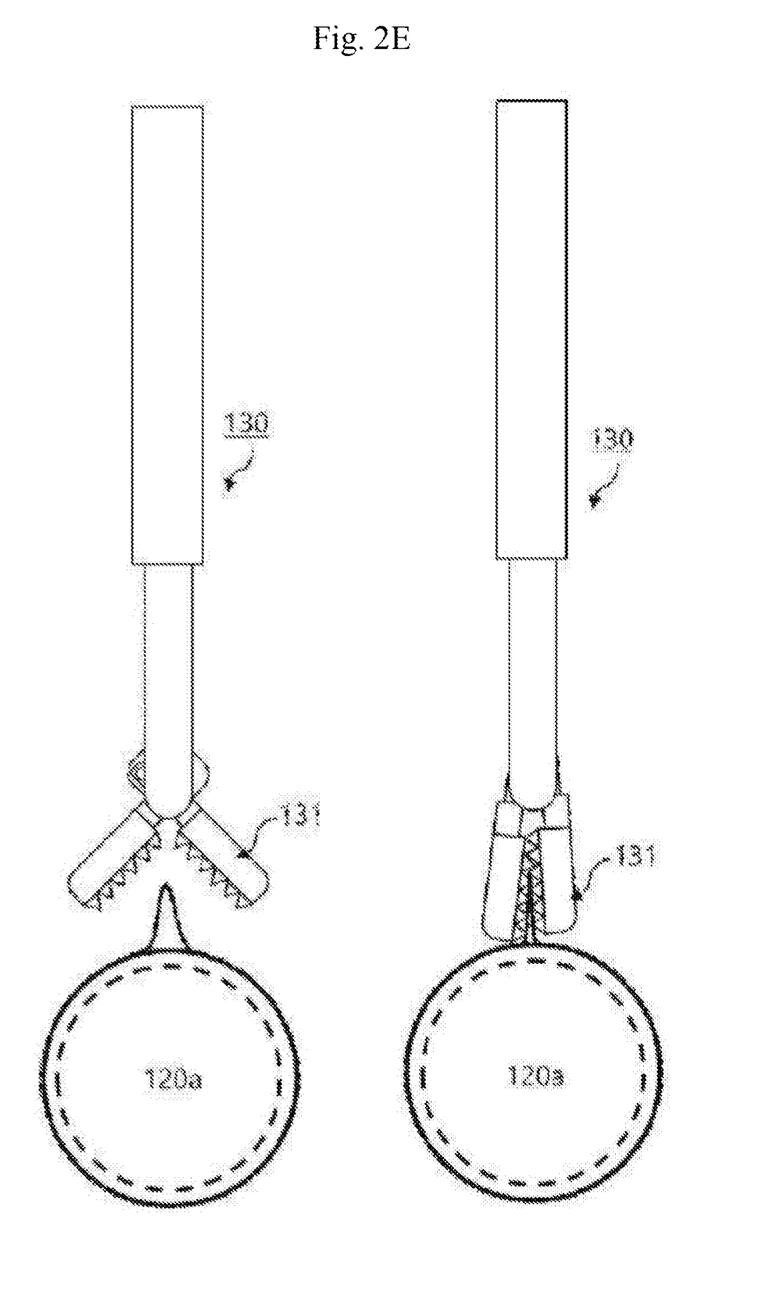

FIG. 2C and FIG. 2D are views for explaining the second sphere (120a) constituting the magnet assembly apparatus according to another embodiment of the present invention. FIG. 2E is a view for explaining how the second sphere (120a) of FIG. 2C and FIG. 2D is used. In FIG. 2C and FIG. 2D, the second sphere (120a) further includes a holding portion (121). The holder (121) is a portion that can hold the second sphere (120a) from the outside using an endoscope or the like. The height of the holder is preferably between 3.0 mm and 4.0 mm. The height (t) of the holder (121) may be preferably about 3.5 mm, which is generally the size of a forceps.

Referring to FIG. 2E, the forceps (131) of the endoscope (130) holds the holding portion (121) of the second sphere (120a). Since the forceps (131) of the endoscope is easy to control, it is possible to securely move the second sphere (120a) to the stomach of the human body.

FIG. 3A and FIG. 3B illustrate a magnet assembly apparatus (100) according to an embodiment of the present invention. As illustrated, the first sphere (110) and the second sphere (120) gathered to form a magnet assembly apparatus (100) according to an embodiment of the present invention. FIG. 3A is a cross sectional view of a magnet assembly apparatus (100) formed by cohesion of a first sphere (110) and a second sphere (120). FIG. 3B is a front view of the magnet assembly apparatus (100) formed by the combination of the first sphere (110) and the second sphere (120). The first and second spheres (110 and 120) are gathered by the mutual magnetic force and at least one or more first spheres (110) may be aggregated around the second sphere (120).

The combined first (110) and second (120) spheres cannot pass through the pylorus and are present within the stomach, reducing the stomach volume of the patient and providing the effect of reduced food intake and weight loss.

Thereafter, the magnetic force of the second sphere (120) is lost over a predetermined period of time, so the coalescence state of the first sphere (110) and the second sphere (120) can be released. For example, a magnetic body that loses its magnetic force when a predetermined time passes may be used as the second sphere (120), or the magnetic force of the second sphere (120) may be controlled inside or outside so that the coalescence state of the first sphere (110) and the second sphere (120) can be released.

When the coalescence state of the first (110) and second sphere (120) is released, the first sphere (110) is discharged out of the body through the large intestine. The second sphere (120) can be removed out of the body of the patient using an endoscope thorough the esophagus.

A Method of Using the Magnet Assembly Apparatus

A method of using the magnet assembly apparatus according to an embodiment of the present invention will be described with reference to FIG. 4 and FIG. 5.

FIG. 4 is a flowchart of a method of using a magnet assembly apparatus according to one embodiment of the present invention. First, a first sphere (110) is injected into the patient's stomach (S100). As described above, since the diameter ($r\_1$) of the first sphere (110) is smaller than the diameter of the human esophagus, the first sphere (110) may be injected into the patient's stomach, for example, by the patient taking the first sphere (110) orally. At this time, the patient can take at least one of the first spheres (110), and the number of the first spheres (110) to be taken can be appropriately selected on the basis of the physical condition of the person, the degree of obesity, the target weight value, etc.

After injecting the first sphere (110), a second sphere (120) is injected into the patient's stomach (S110). As described above, it is preferable that the diameter of the second sphere (120) is larger than the diameter of the first sphere (110). And, the size of the second sphere (120) is preferably such that it can be injected orally through an endoscope. Particularly, the diameter of the second sphere (120) is preferably 2 cm. The endoscope can be used to inject the second sphere (120) through the patient's mouth and esophagus into the stomach.

The first sphere (110) and the second sphere (120) are agglomerated in a state where the first sphere (110) and the second sphere (120) are injected into the stomach (S120). The first sphere (110) and the second sphere (120) are aggregated to form a magnet assembly apparatus (100) according to an embodiment of the present invention. The first and second spheres (110, 120) are aggregated by the mutual magnetic force and at least one or more first spheres (110) may be aggregated around the second sphere (120). The aggregated first and second spheres (110 and 120) can not pass through the pylorus and are present in the stomach.

Next, it is determined whether a predetermined time has passed (S130). For example, the predetermined time may be set to 6 months, but the present invention is not limited thereto and may be set differently for each patient based on the patient's physical condition, obesity degree, target weight, target body fat, target BMI, etc.

When the predetermined time has elapsed, the cohesion of the first and second spheres (110 and 120) is released (S140). For example, a magnetic material which loses its magnetic force when a predetermined time elapses is used as the second sphere (120), so that mutual magnetic force between the first sphere (110) and the second sphere (120) is released when a predetermined time elapses, and the agglomeration of the first sphere (110) and the second sphere (120) can be released.

Alternatively, the magnetic force of the second sphere (120) may be controlled internally and/or externally to release the cohesion state of the first sphere (110) and the second sphere (120). As an example of internal control of the magnetic force of the second sphere (120), an internal switch (not shown), which operates to enclose the magnetic force shielding material on the second sphere (120), can be installed. When the internal switch is turned on, the magnetic force shielding material can enclose the outer surface of the second sphere (120). The magnetic force shielding material wrapped around the outer surface of the second sphere (120) can release mutual magnetic force between the first sphere (110) and the second sphere (120) by encapsulating the second sphere (120). At this time, ON/OFF control of the internal switch can be performed by a short-range wireless communication method such as Bluetooth, etc.

Specifically, the second sphere may include a battery and a magnetic force generating device which generates a magnetic force inside. If the life cycle of the battery is set according to the period during which the magnetic device is to be held in the stomach, the life time of the battery is automatically completed when the set time comes, and the mutual magnetic force of the first and second spheres (110 and 120) is lost so that the first sphere (110) and the second sphere (120) are separated and automatically pass through the pylorus.

In addition, in some cases, the apparatus may further include a wireless communication switching unit so that the apparatus is controllable by wireless communication from the outside. For example, the magnetic force formation can be controlled from the outside by wireless communication such as Bluetooth. For example, if the target weight is reached or the required period is exceeded, the first and second spheres (110 and 120) can be separated by external controlling.

Also, as an example in which the magnetic force of the second sphere (120) is externally controlled, the mutual magnetic force between the first sphere (110 and 120) may be controlled by an external magnetic field. In this case, it is preferable that the second sphere (120) is made of a component of a superparamagnetism. Superparamagnetism is a substance whose magnetization disappears due to thermal motion when an external magnetic field is not applied, whereas the degree of magnetization induced when an external magnetic field is applied is much larger than that of a paramagnetic substance. Superparamagnetic material is a material that exhibits magnetic saturation phenomenon similar to ferromagnetic material in the critical magnetic field. Generally, when the particle size of the ferromagnetic substance is from several to several hundred nanometers, the phase transition can be made to a superparamagnetic material. For example, in the case of iron oxide, it may have a superparamagnetic property at a size of about 10 nm. Unlike the ferromagnetic material, which retains magnetism even when the magnetic field is removed, the super-magnetic material is magnetized only when an external magnetic field is present. Accordingly, by applying an external magnetic field, the second sphere (120) is magnetized to cohere the first sphere (110) and the second sphere (120), or conversely, by removing an external magnetic field applied, the cohesion of the first sphere (110) and the second sphere (120) can be released.

Meanwhile, although not shown, after the step (S120) of agglomerating the first and second spheres (110, 120), the method may further comprise a step (S125) of wrapping the agglomerated first and second spheres (110, 120) with the silicone mesh. An exemplary silicone mesh (200) is shown in FIG. 5. The silicone net (200) may comprise a silicon coated paper (210) having a void space therein and a wire (220) on the silicone coated paper (210). The silicone coated paper (210) can be formed in net shape. The wire (220) is connected to a tightening device (230). After positioning the magnet assembly apparatus (100) in which the first and second spheres (110, 120) are aggregated in the empty space of the silicon coated paper (210) using an endoscope, the magnet assembly apparatus (100) can be wrapped by the silicon mesh (200) by tightening the wire (200) using the tightening apparatus (230).

For example, the silicon net (200) may be made of a material that can be melted by the gastric secretion. So, the silicon net (200) can position the apparatus in the stomach at the beginning of the procedure, and can naturally dissolve after a certain period of time.

Figure 6A:
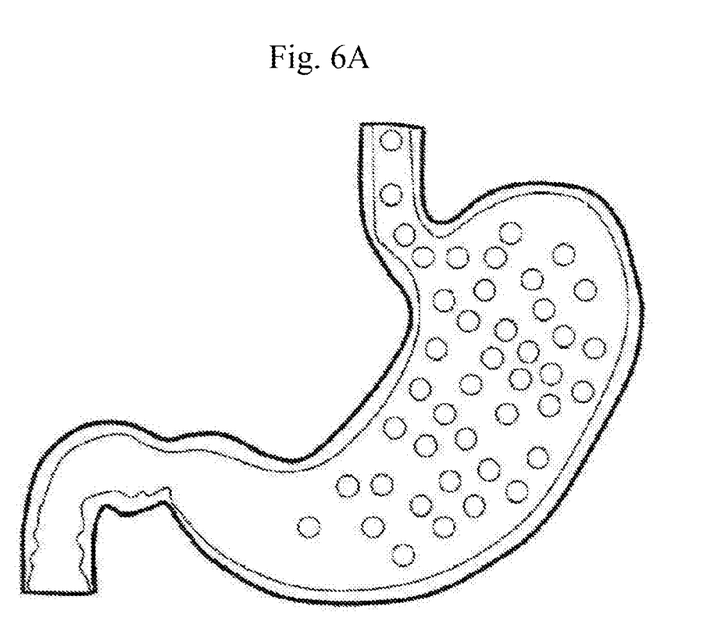
FIGS. 6A, 6B, 6C, 6D, and 6E are schematic views illustrating a method of using the magnet assembly apparatus according to an embodiment of the present invention.
Figure 6B:
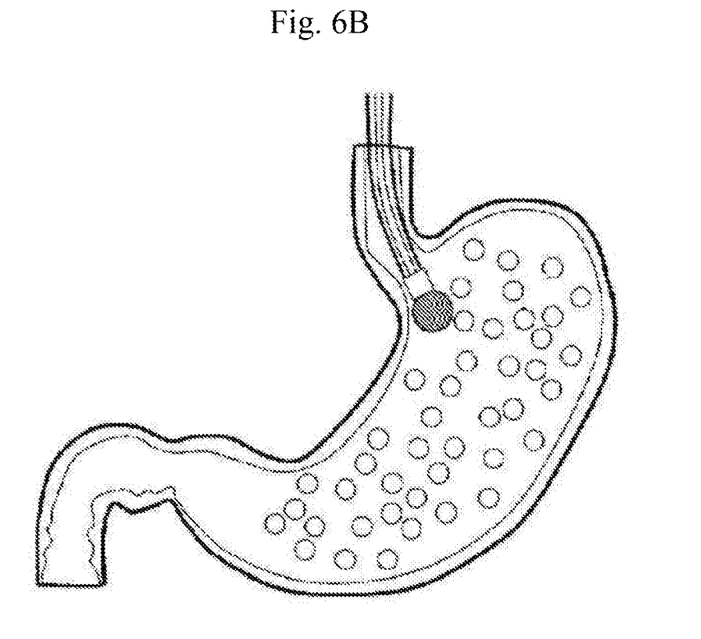
Figure 6C:
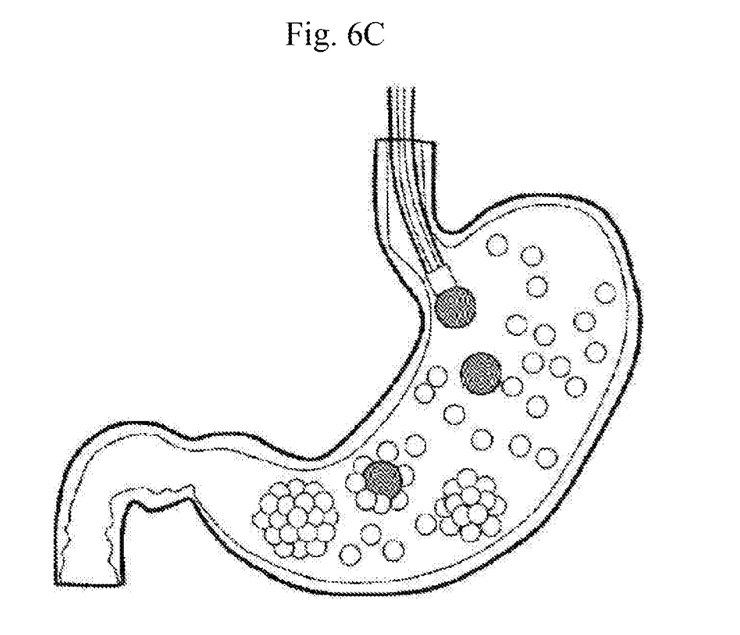
Figure 6D:
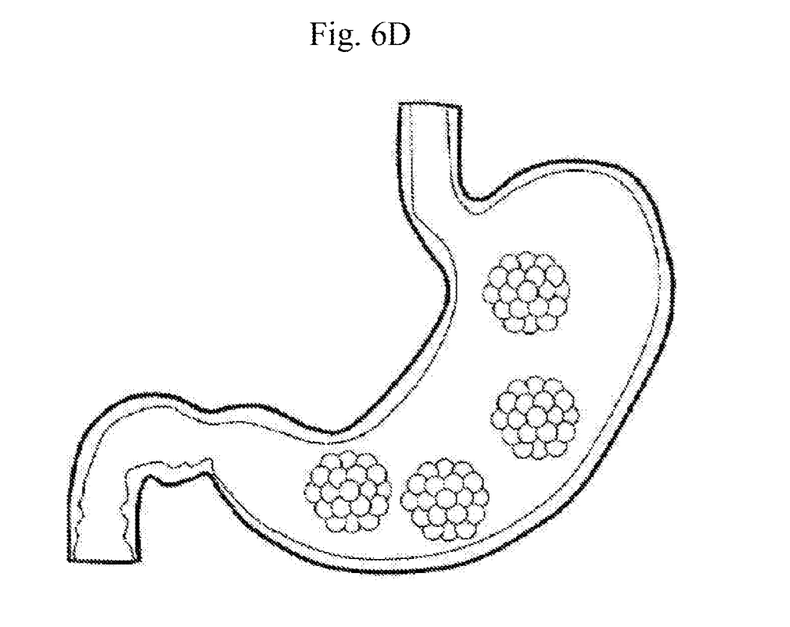
Figure 6E:
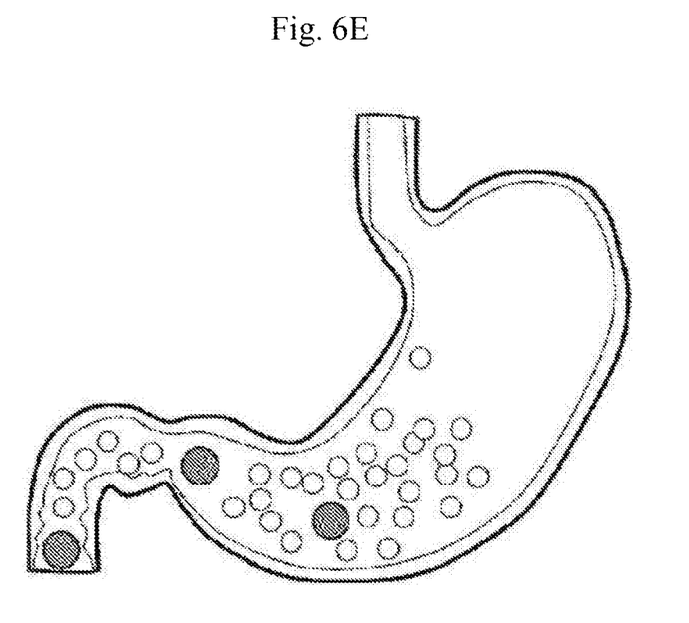

FIG. 6A to FIG. 6E schematically illustrate a method of using the magnet assembly apparatus according to an embodiment of the present invention described with reference to FIG. 4. FIG. 6A illustrates injecting the first sphere (110) into the patient's stomach. FIG. 6B illustrates injecting the second sphere (120) into the patient's stomach using an endoscope. FIG. 6C illustrates that the first and second spheres (110,120) are being gathered by the mutual magnetic force in a state where the first and second spheres (110, 120) are injected in the stomach. FIG. 6D illustrates that the first and second spheres (110 and 120) are combined to form the magnet assembly apparatus (120). FIG. 6E shows a process in which the first sphere (110) and the second sphere (120) are separated from each other after the loss of the magnetic force, and then go out of the body through the pylorus. The details of the subsequent steps have been described with reference to FIG. 4, and will not be described here again.

As described above, according to the magnet assembly apparatus of the present invention, it is possible to treat obesity in a simple, convenient, safe and non-invasive manner. In addition, according to the present invention, unlike surgical treatment, immediate daily life is possible without having to be hospitalized. And, according to the present invention, weight loss can be achieved naturally by suppressing the appetite by increasing the satiety feeling and the yo-yo phenomenon can be minimized.

While the invention has been shown and described with reference to certain preferred embodiments thereof, it will be understood by those skilled in the art that various changes and modifications can be made without departing from the spirit and scope of the invention as defined by the appended claims. Accordingly, the true scope of the present invention should be determined by the following claims.

100: a magnet assembly apparatus
110: a first sphere
120: a second sphere
200: silicon mesh
210: silicon coated paper
220: wire
230: a tightening apparatus

What is claimed is:

1. A magnet assembly apparatus for obesity treatment which can be injected by an oral approach into the stomach of a patient, the apparatus comprises: a first sphere having a first diameter and silicon-coated on the outside, the first sphere configured to be a metal sphere; and a second sphere configured to be a magnetic material, the second sphere having a second diameter bigger than the first diameter, which is a magnetic substance having a magnetic force of a predetermined value, wherein the first and the second spheres are gathered by mutual magnet force to form the magnet assembly apparatus having a size that does not pass through the pylorus, and when the magnet force of the second sphere is lost, the aggregation of the first sphere and the second sphere is released, and the first sphere is discharged to the outside of the a body through the large intestine; and wherein the gathered first and second spheres are wrapped by medical silicon net.

2. The apparatus of claim 1, wherein the first diameter is 1.2 cm and the second diameter is 2 cm.

3. The apparatus of claim 1, wherein the medical silicon net is formed of an automatically melting material in the body after a predetermined time.

4. The apparatus of claim 1, wherein the second sphere comprises a battery and a magnetic force generating device inside, and when the set time comes, the voltage of the battery drops below the threshold voltage that generates a magnetic force capable of combining the first and second spheres.

5. The apparatus of claim 1, wherein the second sphere comprises a holding portion formed protrude from the outer surface of the second sphere, and the holding portion can be caught by a forceps of an endoscope.

6. The apparatus of claim 5, wherein the height of the holding portion is between 3.0 mm and 4.0 mm.

* * * * *